United States Patent
Beaurain et al.

(10) Patent No.: US 9,326,795 B2
(45) Date of Patent: May 3, 2016

(54) IMPLANT FOR OSSEOUS ANCHORING WITH POLYAXIAL HEAD

(75) Inventors: Jacques Beaurain, Saulon la Chapelle (FR); Joel Delecrin, Vertou (FR); Herve Chataigner, Boussieres (FR)

(73) Assignee: LDR Medical, Rosieres Pres Troyes (FR)

( * ) Notice: Subject to any disclaimer, the term of this patent is extended or adjusted under 35 U.S.C. 154(b) by 663 days.

(21) Appl. No.: 10/498,234

(22) PCT Filed: Dec. 12, 2002

(86) PCT No.: PCT/IB02/05302
§ 371 (c)(1),
(2), (4) Date: Dec. 7, 2004

(87) PCT Pub. No.: WO03/049629
PCT Pub. Date: Jun. 19, 2003

(65) Prior Publication Data
US 2005/0107788 A1    May 19, 2005

(30) Foreign Application Priority Data
Dec. 12, 2001   (FR) .................................. 01 16122

(51) Int. Cl.
*A61B 17/04* (2006.01)
*A61B 17/86* (2006.01)
(Continued)

(52) U.S. Cl.
CPC ........... *A61B 17/7034* (2013.01); *A61B 17/701* (2013.01); *A61B 17/7037* (2013.01); *A61B 17/6483* (2013.01); *A61B 17/7004* (2013.01)

(58) Field of Classification Search
USPC ............................................... 606/61, 72, 73
See application file for complete search history.

(56) References Cited

U.S. PATENT DOCUMENTS

| 4,041,939 A | 8/1977 | Hall |
| 4,047,524 A | 9/1977 | Hall |

(Continued)

FOREIGN PATENT DOCUMENTS

| CA | 1304267 | 6/1992 |
| CA | 2443215 | 10/2002 |

(Continued)

OTHER PUBLICATIONS

A unique self-contained connexion; Website: www.ldrmedical.dr/connexion_uk.htm; Oct. 11, 2004.
(Continued)

*Primary Examiner* — Sameh Boles
(74) *Attorney, Agent, or Firm* — Denko Lauff LLP

(57) ABSTRACT

An osseous anchorage implant comprising an attachment structure adapted to receive and be attached to at least one bar, that is suitably an element of an osteosynthesis. The implant is made up of an osseous anchor and an attachment head bearing the attachment means. The attachment head is suitably traversed by a channel that is adapted to receive the bar. The attachment head comprises a clamp that is adapted to clamp the bar against an inside support wall of the channel. The implant is further characterized by the attachment means and the support wall enabling the rotation of the bar about a first axis that is not parallel to the longitudinal axis of the bar. The clamp comprises a moving clamping face, that is adapted to contact the bar, and that is borne by a support head that is articulatable at the end of the clamp via a ball and socket connection. The channel is suitably an open channel having an aperture opening onto one of the lateral faces of the attachment head, wherein the aperture bears the clamp. The bar is enabled to be introduced into the channel from a side of the channel.

25 Claims, 8 Drawing Sheets

(51) Int. Cl.
*A61F 2/08* (2006.01)
*A61B 17/70* (2006.01)
*A61B 17/64* (2006.01)

(56) References Cited

U.S. PATENT DOCUMENTS

| | | | |
|---|---|---|---|
| 4,055,385 A | 10/1977 | Bjors | |
| 4,429,690 A | 2/1984 | Angelino-Pevani | |
| 4,648,388 A | 3/1987 | Steffee | |
| 4,653,481 A | 3/1987 | Howland et al. | |
| 4,696,290 A | 9/1987 | Steffee | |
| 4,773,402 A | 9/1988 | Asher et al. | |
| 4,946,458 A | 8/1990 | Harms et al. | |
| 5,024,213 A | 6/1991 | Asher et al. | |
| 5,067,955 A | 11/1991 | Cotrel | |
| 5,092,893 A | 3/1992 | Smith | |
| 5,129,899 A | 7/1992 | Small et al. | |
| 5,176,680 A | 1/1993 | Vignaud et al. | |
| 5,197,986 A | 3/1993 | Mikhail | |
| 5,226,766 A | 7/1993 | Lasner | |
| 5,269,784 A | 12/1993 | Mast | |
| 5,275,600 A | 1/1994 | Allard et al. | |
| 5,282,863 A | 2/1994 | Burton | |
| 5,314,477 A | 5/1994 | Marnay | |
| 5,330,473 A | 7/1994 | Howland | |
| 5,344,421 A | 9/1994 | Crook et al. | |
| 5,358,526 A | 10/1994 | Tornier | |
| 5,374,267 A | 12/1994 | Siegal | |
| 5,401,269 A | 3/1995 | Buttner-Janz et al. | |
| 5,437,669 A | 8/1995 | Yuan et al. | |
| 5,456,698 A | 10/1995 | Byland et al. | |
| 5,486,174 A | 1/1996 | Fournet-Fayard et al. | |
| 5,486,176 A | 1/1996 | Hildebrand et al. | |
| 5,501,684 A | 3/1996 | Schlapfer | |
| 5,520,689 A * | 5/1996 | Schlapfer et al. | 606/270 |
| 5,531,747 A | 7/1996 | Ray | |
| 5,536,268 A * | 7/1996 | Griss | 606/254 |
| 5,545,163 A | 8/1996 | Miller et al. | |
| 5,545,167 A | 8/1996 | Lin | |
| 5,578,033 A * | 11/1996 | Errico et al. | 606/61 |
| 5,582,612 A | 12/1996 | Lin | |
| 5,584,833 A | 12/1996 | Fournet-Fayard et al. | |
| 5,584,834 A | 12/1996 | Errico et al. | |
| 5,591,166 A | 1/1997 | Bernhardt et al. | |
| 5,601,552 A | 2/1997 | Cotrel | |
| 5,603,714 A * | 2/1997 | Kaneda et al. | 606/272 |
| 5,609,592 A | 3/1997 | Brumfield et al. | |
| 5,613,968 A | 3/1997 | Lin | |
| 5,620,443 A | 4/1997 | Gertzbein et al. | |
| 5,628,740 A | 5/1997 | Mullane | |
| 5,651,789 A | 7/1997 | Cotrel | |
| 5,725,528 A * | 3/1998 | Errico et al. | 606/61 |
| 5,733,286 A | 3/1998 | Ralph et al. | |
| 5,735,851 A | 4/1998 | Errico et al. | |
| 5,743,907 A | 4/1998 | Asher et al. | |
| 5,743,911 A | 4/1998 | Cotrel | |
| RE35,784 E | 5/1998 | Linkow et al. | |
| 5,797,911 A | 8/1998 | Sherman et al. | |
| 5,800,435 A * | 9/1998 | Errico et al. | 606/61 |
| 5,876,403 A | 3/1999 | Shitoto | |
| 5,899,903 A | 5/1999 | Cotrel | |
| 5,910,142 A * | 6/1999 | Tatar | 606/61 |
| 5,938,663 A * | 8/1999 | Petreto | 606/61 |
| 5,947,965 A | 9/1999 | Bryan | |
| 5,947,966 A | 9/1999 | Drewry et al. | |
| 5,951,557 A | 9/1999 | Luter | |
| 5,984,928 A | 11/1999 | Hermann | |
| 5,989,250 A | 11/1999 | Wagner et al. | |
| 5,989,254 A * | 11/1999 | Katz | 606/73 |
| 6,030,389 A | 2/2000 | Wagner et al. | |
| 6,045,552 A | 4/2000 | Zucherman et al. | |
| 6,053,921 A | 4/2000 | Wagner et al. | |
| 6,063,090 A | 5/2000 | Schlaepfer | |
| 6,066,140 A | 5/2000 | Gertzbein et al. | |
| 6,074,393 A | 6/2000 | Sitoto | |
| 6,077,262 A * | 6/2000 | Schlapfer et al. | 606/61 |
| 6,083,224 A | 7/2000 | Gertzbein et al. | |
| 6,113,601 A * | 9/2000 | Tatar | 606/61 |
| 6,117,135 A | 9/2000 | Schlapfer | |
| 6,123,706 A * | 9/2000 | Lange | 606/61 |
| 6,129,730 A | 10/2000 | Bono et al. | |
| 6,132,430 A | 10/2000 | Wagner | |
| 6,136,000 A | 10/2000 | Louis et al. | |
| 6,136,002 A | 10/2000 | Shih et al. | |
| 6,206,879 B1 | 3/2001 | Marnay et al. | |
| 6,214,012 B1 | 4/2001 | Karpman et al. | |
| RE37,161 E | 5/2001 | Michelson et al. | |
| 6,235,034 B1 | 5/2001 | Bray | |
| 6,248,104 B1 | 6/2001 | Chopin et al. | |
| 6,248,105 B1 | 6/2001 | Shlapfer et al. | |
| 6,254,603 B1 | 7/2001 | Gertzbein et al. | |
| 6,261,288 B1 | 7/2001 | Jackson | |
| 6,267,765 B1 | 7/2001 | Taylor et al. | |
| 6,277,119 B1 | 8/2001 | Walulik et al. | |
| 6,280,445 B1 | 8/2001 | Morrison et al. | |
| 6,287,309 B1 | 9/2001 | Baccelli et al. | |
| 6,306,136 B1 | 10/2001 | Baccelli | |
| 6,344,057 B1 | 2/2002 | Rabbe et al. | |
| 6,355,038 B1 | 3/2002 | Phisharodi | |
| 6,391,030 B1 | 5/2002 | Wagner et al. | |
| 6,413,259 B1 | 7/2002 | Lyons et al. | |
| 6,416,515 B1 | 7/2002 | Wagner | |
| 6,454,769 B2 | 9/2002 | Wagner et al. | |
| 6,458,132 B2 | 10/2002 | Choi | |
| 6,471,704 B2 | 10/2002 | Gertzbein et al. | |
| 6,475,218 B2 | 11/2002 | Gournay et al. | |
| 6,478,798 B1 | 11/2002 | Howland | |
| 6,488,682 B2 | 12/2002 | Kikuchi et al. | |
| 6,506,216 B1 | 1/2003 | McCue et al. | |
| 6,547,790 B2 | 4/2003 | Harkey, III et al. | |
| 6,551,322 B1 | 4/2003 | Lieberman | |
| 6,554,831 B1 | 4/2003 | Rivard et al. | |
| 6,554,834 B1 * | 4/2003 | Crozet et al. | 606/65 |
| 6,562,040 B1 | 5/2003 | Wagner | |
| 6,565,565 B1 | 5/2003 | Yuan et al. | |
| 6,565,605 B2 | 5/2003 | Goble et al. | |
| 6,579,319 B2 | 6/2003 | Goble et al. | |
| 6,585,738 B1 | 7/2003 | Mangione et al. | |
| 6,595,992 B1 | 7/2003 | Wagner et al. | |
| 6,602,254 B2 | 8/2003 | Gertzbein et al. | |
| 6,610,063 B2 | 8/2003 | Kumar et al. | |
| 6,613,050 B1 | 9/2003 | Wagner et al. | |
| 6,613,053 B1 | 9/2003 | Collins et al. | |
| 6,616,664 B2 | 9/2003 | Walulik et al. | |
| 6,620,164 B2 | 9/2003 | Ueyama et al. | |
| 6,626,904 B1 | 9/2003 | Jammet et al. | |
| 6,641,583 B2 | 11/2003 | Shluzas et al. | |
| 6,641,585 B2 | 11/2003 | Sato et al. | |
| 6,641,586 B2 | 11/2003 | Varieur | |
| 6,663,631 B2 | 12/2003 | Kuntz | |
| 6,669,697 B1 | 12/2003 | Pisharodi | |
| 6,682,530 B2 | 1/2004 | Dixon et al. | |
| 6,682,533 B1 | 1/2004 | Dinsdale et al. | |
| 6,702,814 B2 | 3/2004 | Walulik et al. | |
| 6,702,815 B2 | 3/2004 | Kuntz | |
| 6,726,687 B2 | 4/2004 | Jackson | |
| 6,736,816 B2 * | 5/2004 | Ritland | 606/61 |
| 6,749,613 B1 | 6/2004 | Conchy et al. | |
| 6,755,829 B1 | 6/2004 | Bono et al. | |
| 6,884,241 B2 | 4/2005 | Bertranou et al. | |
| 2001/0001119 A1 | 5/2001 | Lombardo | |
| 2001/0010000 A1 | 7/2001 | Gertzbein et al. | |
| 2001/0047173 A1* | 11/2001 | Schlapfer et al. | 606/72 |
| 2002/0010467 A1* | 1/2002 | Cooper et al. | 606/61 |
| 2002/0013585 A1 | 1/2002 | Gournay et al. | |
| 2002/0193795 A1 | 12/2002 | Gertzbein et al. | |
| 2003/0045875 A1 | 3/2003 | Bertranou et al. | |
| 2003/0088251 A1 | 5/2003 | Braun et al. | |
| 2003/0114853 A1 | 6/2003 | Burgess et al. | |
| 2003/0187441 A1 | 10/2003 | Bolger et al. | |
| 2004/0158251 A1 | 8/2004 | Morrison et al. | |
| 2004/0172020 A1 | 9/2004 | Beaurain et al. | |

(56) References Cited

U.S. PATENT DOCUMENTS

| | | |
|---|---|---|
| 2004/0254577 A1 | 12/2004 | Delecrin et al. |
| 2005/0010215 A1 | 1/2005 | Delecrin et al. |
| 2005/0107788 A1 | 5/2005 | Beaurain et al. |

FOREIGN PATENT DOCUMENTS

| | | |
|---|---|---|
| DE | 4201043 A | 7/1993 |
| DE | 19512709 A | 10/1996 |
| DE | 19545612 A | 6/1997 |
| DE | 196 05 640 A | 8/1997 |
| DE | 19605640 A | 8/1997 |
| EP | 0274713 A | 7/1988 |
| EP | 0301489 A | 2/1989 |
| EP | 0490812 A | 6/1992 |
| EP | 0 572 790 A | 12/1993 |
| EP | 0572790 A | 12/1993 |
| EP | 0679369 A | 11/1995 |
| EP | 0846444 | 6/1998 |
| EP | 1254640 A | 11/2002 |
| FR | 2659226 A | 9/1991 |
| FR | 2683445 | 5/1993 |
| FR | 2697993 | 5/1994 |
| FR | 2702361 A | 9/1994 |
| FR | 2704136 | 10/1994 |
| FR | 2706763 A | 12/1994 |
| FR | 2724108 A | 3/1996 |
| FR | 2726171 A | 5/1996 |
| FR | 2735011 | 12/1996 |
| FR | 2765093 A | 12/1998 |
| FR | 2823095 | 4/2001 |
| FR | 2827150 A | 1/2003 |
| FR | 2831048 | 4/2003 |
| FR | 2831049 | 4/2003 |
| FR | 2833151 | 6/2003 |
| FR | 2859095 | 3/2005 |
| GB | 2178323 A | 2/1987 |
| JP | 09098983 A | 4/1997 |
| WO | WO9307823 | 4/1993 |
| WO | 95 10240 A | 4/1995 |
| WO | WO9510240 A | 4/1995 |
| WO | WO9900065 | 1/1999 |
| WO | WO9933405 A | 7/1999 |
| WO | WO9956675 A | 11/1999 |
| WO | WO0015125 A | 3/2000 |
| WO | WO0018312 A | 4/2000 |
| WO | WO0101874 A | 1/2001 |
| WO | WO0103592 A | 1/2001 |
| WO | WO0126566 A | 4/2001 |
| WO | WO0228299 A | 4/2002 |
| WO | WO02080788 | 10/2002 |
| WO | WO03032850 A1 | 4/2003 |
| WO | WO03032851 | 4/2003 |
| WO | WO03039400 A2 | 5/2003 |
| WO | WO03049629 A1 | 6/2003 |
| WO | WO2005020829 A1 | 3/2005 |

OTHER PUBLICATIONS

FR 2 704 136 Preliminary Search Report, National Institute of Industrial Property (France), Nov. 24, 1993.
FR 2 823 095 Preliminary Search Report, National Institute of Industrial Property (France), Dec. 20, 2001.
FR 2 827 150 Preliminary Search Report, National Institute of Industrial Property (France), Apr. 8, 2002.
FR 2 831 048 Preliminary Search Report, National Institute of Industrial Property (France), Jul. 3, 2002.
FR 2 831 049 Preliminary Search Report, National Institute of Industrial Property (France), Jul. 3, 2002.
FR 2 831 796 Preliminary Search Report, National Institute of Industrial Property (France), Aug. 2, 2002.
FR 2 833 151 Preliminary Search Report, National Institute of Industrial Property (France), Aug. 28, 2002.
FR 2 859 095 Preliminary Search Report, National Institute of Industrial Property (France), Apr. 14, 2004.
PCT/FR98/01363 (Publication WO9900065 Jan. 7, 1999), International Search Report, EPO, Oct. 14, 1998.
PCT/IB02/02827 International Search Report, EPO, Oct. 4, 2002.
PCT/IB02/04306 International Search Report, EPO, Feb. 4, 2003.
PCT/IB02/04307 International Search Report, EPO, Feb. 4, 2003.
PCT/IB02/04642 International Search Report, EPO, Jul. 2, 2003.
PCT/IB02/05302 International Search Report, EPO, Mar. 25, 2003.
PCT/IB04/002825 International Search Report, EPO, Jan. 7, 2005.
PCT/IB02/02827 International Preliminary Examination Report, EPO, May 15, 2003.
PCT/IB02/04306 International Preliminary Examination Report, EPO, Jul. 9, 2003.
PCT/IB02/04307 International Preliminary Examination Report, EPO, Jan. 13, 2004.
PCT/IB02/04642, International Preliminary Examination Report, EPO, Apr. 1, 2004.
PCT/IB02/05302 International Preliminary Examination Report, EPO, Mar. 23, 2004.
PCT/IB04/002825, International Preliminary Report on Patentability, EPO, Oct. 25, 2005.
PCT/IB04/002825, Written Opinion of the International Searching Authority, EPO, Jan. 5, 2005.
Product Bulletin, Acromed Corporation, Date Unknown.
Spinal Instrumentation, An and Cotler, 1992, Williams & Wilkins, pp. 399-400.
Spinal Product Systems, Zimmer, Date Unknown.
Stafix Plate System;Daruma, Date Unknown.
The Syracuse I-Plate, James C. Bayley, Md., et al., Department of Orthopedic Surgery, SUNY-HSC at Syracuse, Spine, vol. 16, No. 3 Supplement, Date Unknown.
TSRH Spinal Implant System, Danek Medical Inc., Date Unknown.
Un nouveau standard: la barre á méplat LDR; Website: www.ldrmedical.fr/easyspine.htm; Sep. 19, 2004.

\* cited by examiner

IMPLANT FOR OSSEOUS ANCHORING WITH POLYAXIAL HEAD

FIELD OF THE INVENTION

The present invention relates to an implant providing osseous anchorage, for example in a vertebra for anchoring an osteosynthesis device. This implant comprises a head capable of receiving a bar linking a plurality of implants in different angular positions.

BACKGROUND OF THE INVENTION

It is known to fix one or a plurality of implants into one or a plurality of osseous elements in order to connect to the skeleton a device implanted in the human or animal body, said implants being then used to fasten certain elements of said device. For maintaining or correcting the rachis in particular, use of an osteosynthesis device comprising one or a plurality of maintenance bars or plates positioned along the vertebral column and fixed to certain vertebrae by implants is well-known. These implants are fixed on the one hand to the bars and on the other to the vertebrae by an osseous anchoring means comprised of a hook having its support on a vertebra or of a threaded part screwed inside the vertebra, for example, at the pedicle. In the case of an osteosynthesis of the extreme vertebrae one or a plurality of implants can of course be securely fastened to adjacent bone, the sacrum for example.

The FR 0104717 patent discloses for this purpose an implant comprising an osseous anchoring part and a fixation head traversed by a channel where the bar is clamped. This document describes an implant, whose head comprises a lateral opening enabling the introduction of a bar with flat areas wherein a clamping screw has already been pre-installed in the superior part of said head. In order to assure satisfactory contact of the clamping screw on the flat surface whatever the angular position of said flat surface about the axis of the pin, the clamping screw is provided with a tiltable support surface mounted on a ball and socket joint.

By supporting itself on the inside shape of the channel under the effect of the clamping, the bar's position is thus definitively determined by the general position of the implant. At the time of attachment of the bar to an implant that is already anchored in the rachis, if the bar is not in a position corresponding to that of the channel, the act of forcing its introduction can induce a certain stress in the bar.

On the one hand, said stress can then make the attachment of the bar to the implant difficult or render its clamping not very accurate. This problem is true more particularly when the bar has already been engaged with a first implant and is being attached to a second implant. In order to reduce this stress, it is conceivable to anchor the implant according to the position of the bar, but this is not always possible to do nor easy to predict. It would also be conceivable to deform the bar, which could be a problem in the situation and plays against the requirement of a rigid bar to assure an effective hold. This stress can thus make manipulation delicate to execute, in particular in weale intrusion surgical procedures, for example video-assisted or laparoscopic procedures.

On the other hand, even if clamping enables stressing the bar to adopt a position or a shape corresponding to the implant, said stress will persist permanently over a very long time after the procedure. The fact that the bar is under permanent stress poses the risk of a mechanical effect directly on the rachis, for example causing pains or changing or disturbing the correction or the support sought by using the osteosynthesis device.

OBJECTS AND GENERAL DESCRIPTION OF THE INVENTION

An object of the present invention is to eliminate at least one drawback of the prior art by providing an osseous anchorage implant capable of adapting itself, at least to a certain extent, to different orientations of the bar when the implant is already anchored in the osseous element.

This object is achieved by an implant for osseous anchoring comprising a fixation structure that is capable of receiving and fixing at least one bar, in particular a bar of an osteosynthesis device. The implant comprises on the one hand an osseous anchoring structure, and on the other hand a fixation head bearing the fixation means. The fixation head is traversed by at least one channel that is adapted to receive the bar. The structure further comprises a clamp adapted to clamp the bar against one inside wall of the channel, called a support wall. The implant is characterized in that the fixation structure and the support wall enable obtaining, prior to locking the fixation structure in place, a pre-determined clearance in rotation around at least one first axis that is not parallel to the longitudinal axis of the bar. The clamp comprises a face that is adapted to be in contact with the bar, called a moving clamping face. The moving clamping face of the clamp is borne by a support head articulated at the end of the clamp by means of a ball and socket connection. The channel has the form of an open channel having an aperture opening onto one of the lateral faces of the fixation head, wherein one edge of said aperture bears the clamp. The-aperture of the channel and the position of the clamp thus enable introduction of the bar by a lateral route.

According to another feature, the fixation structure and said support wall enable, prior to blocking the fixation structure, a pre-determined clearance in rotation around at least one second axis not parallel to the first axis and not parallel to the longitudinal axis of the bar.

According to another feature, the channel opens at each side of the fixation head through apertures whose disposition and dimensions enable the bar to have a pre-determined clearance inside the channel in rotation at least about one axis that is substantially perpendicular to the axis of the channel and to the support direction of the clamping means.

According to another feature, the support wall comprises an element, called a moving baseplate, having a clearance in rotation at least about one axis not parallel to the axis of the channel and to the support direction of the clamping means on the bar, the moving clamping face having a determined clearance in rotation around one axis substantially parallel to the axis of rotation of the moving baseplate.

According to another feature, the moving baseplate has a part in the form of a spherical portion supported by means of a complementary contact in a housing formed in the fixation head.

According to another feature, the moving baseplate is in contact with the bar through a support face having a shape that is substantially complementary to the exterior shape of the bar. The moving baseplate comprises at least one formal irregularity that is adapted to co-operate with a formal irregularity borne by the fixation head to form a stop that is adapted to hold the support face of the baseplate turned towards the side of the bar.

According to another feature, the formal irregularity is a pin disposed on the underside, the rear or on the front of the moving baseplate, adapted to cooperate with a cavity with a greater dimension that is borne by the fixation head.

According to another feature, the formal irregularity is a cylindrical hole, preferably drilled, disposed on the front of the moving baseplate and adapted to cooperate with the cylindrical head of a pin held in hole formed in the fixation head.

According to another feature, the clamp comprises a clamping screw inserted into a hole that is traversing to one edge of the channel opening and is adapted to cooperate with said drilled hole to produce a support for the bar.

According to another feature, the osseous anchor comprise either a threaded part capable of anchoring in an osseous element by co-operation with the osseous material of said osseous element, or a protruding part capable of anchoring at the surface of an osseous element by co-operating with at least one formal irregularity of said same surface.

According to another feature, the osseous anchor comprises an elongated and threaded part, the axis of the channel being substantially perpendicular to the longitudinal axis of the osseous anchor.

According to another feature, the channel has a shape comprising two head to tail truncated cones with their minor baseplates facing each other and joined to each other directly or by means of a cylindrical part.

According to another feature, the bar bears one or a plurality of flat areas on its external surface, whereby providing a flat contact surface for the support head.

The invention together with its features and advantages will be clearer by reading the description thereafter with reference to the annexed drawings, wherein:

BRIEF DESCRIPTION OF THE DRAWING

FIGS. 1, 2, and 3 together represent an implant with a moveable head and osseous anchorage;

DETAILED DESCRIPTION OF THE INVENTION

The invention described herein relates to an implant comprising on the one hand a means for holding a bar and on the other hand means for anchoring it to an osseous element.

In a general fashion, in the field of surgery, an implant is defined as an object intended for being implanted in a human or animal body and to remain there continuously after the surgical procedure, at least over a certain period of time. More precisely, one speaks of a prosthesis to designate a device realizing a function, for example a movement or an articulation. Although not comprising a prosthesis per se, it must be understood that the implant described herein can comprise part of a prosthesis device or can be used for attachment of such a device to a structural part of a patient.

By way of example, an implant according to the invention is described herein in the form of an implant incorporated in an osteosynthesis device, such as used to hold, prop, or straighten the rachis. This function is thus assured by one or a plurality of rigid bars or similar elements, connecting a plurality of rachis elements, such as the sacrum, the vertebrae or parts of vertebrae with each other. In the same sense, such a bar can obviously also be used also to connect another implant or prosthesis to a skeleton such as, for example, an artificial vertebra, an arthrodesis frame, or an intervertebral disc prosthesis.

In its part affixed to an osseous element, said bar is functionally attached to an osseous element by means of one or a plurality of implants comprising an osseous anchor such as, for example, a screw or one or a plurality of hooks. The implants thus comprise fixation elements that are adapted to receive-the bar before, or in the course of, a surgical procedure. The-bar is then attached to the implant.

In one embodiment represented in FIGS. 1 to 6, the anchor comprises an elongated part having a thread that is capable of being screwed into the osseous material, for example at the pedicle or body of a vertebra or into the sacrum.

Figure 7:
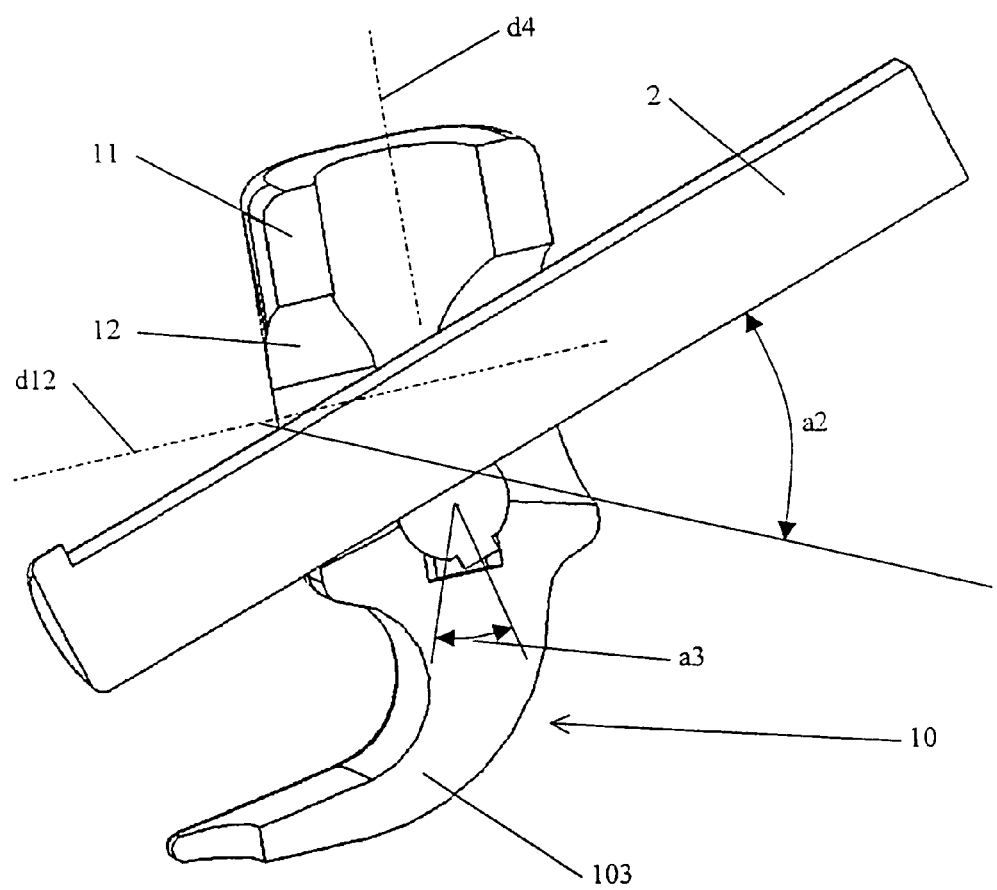
FIG. 7 is a perspective view of an implant that has osseous anchorage by means of a hook and a fixed head in longitudinal section along the axis of the bar and shown without its clamp.
Figure 8:
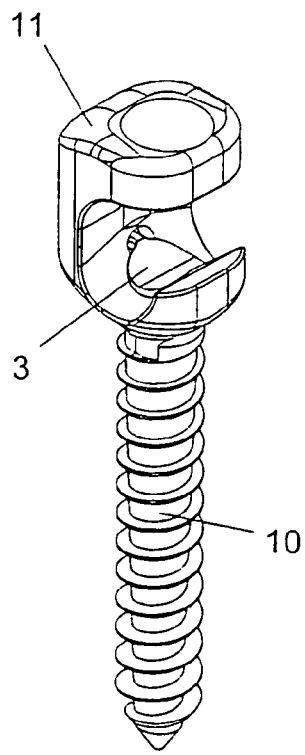
FIGS. 8 and 9 are, respectively, a perspective view and a sectional view of an implant with a fixed head according to a second embodiment of the invention.
Figure 9:
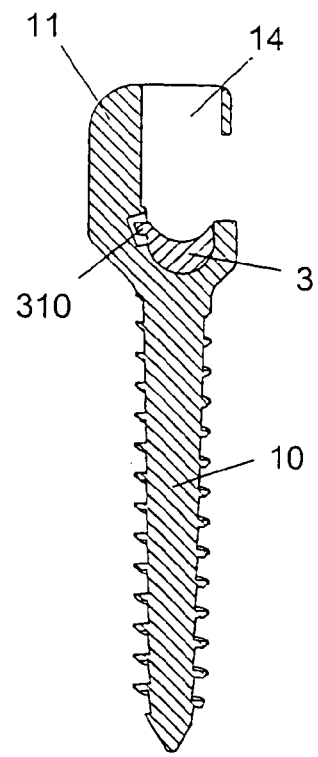

In one embodiment represented in FIG. 7, said osseous anchor comprises a hook that is adapted to engage a formal irregularity in the osseous element, such as a pedicle or a vertebral or sacral protrusion, or a transverse apophysis.

In the course of the surgical procedure, when an implant is anchored in an osseous element and a bar is to be fixed to it, the position in which the bar can be introduced does not always correspond to that which would be the easiest to assemble to the fixation structure of the implant. Said position can be restricted, for example, by the anatomical environment or by the fact that said bar is already attached to another implant.

Moreover, when the bar is inserted into the fixation structure, if the latter is not properly aligned with the axis of the bar, the misalignment of the contact or fixation surfaces can be the cause of poor fixation, such that the attachment is not-sufficiently rigid or secure.

In particular, if the bar must be forced at the time of the attachment to be adapted to be mated with the relative position of the implants, said force can result in residual stresses in the structure of the osteosynthesis device. Such persisting stresses can consequently impair the patient's daily comfort or perturb or change the desired effect of the device.

In order that the attachment element can be better accommodated to the position of the bar, the attachment element according to the invention comprises at least one element having a certain moveability. The position of the moveable element can be adjusted by rotating it around one or a plurality of axes that are not coincident with the longitudinal axis of the bar and, for example, perpendicular to said longitudinal axis of the bar. Said rotation can be executed within a predetermined clearance that is capable of enabling maximum angular positions or according to predetermined angular positions or capable of not being limited, that is completely free of constraints. According to the embodiments, said attachment structure can comprise an element adapted to move along one or a plurality of axes or it may comprise a plurality of elements which are themselves adapted to move along one or a plurality of axes.

The bar can thus be assembled in a plurality of angular positions relative to the anchor or to the osseous element. These variations in angular position can particularly comprise an adjustable tilt relative to the osseous surface to which the implant is anchored or a rotation around an axis extending from said osseous surface or a combination of the two.

In the embodiments represented herein, the implant (1)(see FIG. 5) is rigidly connected to the bar (2) by an attachment structure comprising a channel (12) disposed in one part of the implant, said part being designated as the fixation head (11). The channel (12) can have the shape of a channel that is open at its two ends and open on one of its sides. Such a lateral opening (120) thus enables introduction (see FIG. 4) of the bar (2) through the side of the channel without the necessity of having to thread the bar through an end.

Once inserted into the channel (12), attachment of the bar is assured by a clamp (4) that is supported by means of at least one side of said bar so as to make contact with the bar and force it against a wall, called the support wall, of the channel (12). Said clamp comprises, for example, a clamping screw (41) mounted in a drilled hole (14) borne by one part of the fixation head (11) constituting one edge (124) of the lateral opening (120) of the channel (12). Said clamping screw (41) has an external threading that co-operates with an internal threading of said tapped hole (14) to move the screw (41) along a clamping axis (d4) and bring it into contact against the bar (2), thus clamping the clamping screw (41) to comprise formal irregularities, for example an internal mark, enabling the use of a clamping tool to achieve forcing the bar (2) against a wall. The bar can advantageously have one or a plurality of flat areas upon its external surface in order to enable a flat contact surface to be obtained with the clamping screw (41) and thus the reliability of forcing the bar against the wall is enhanced compared to a punctal or linear contact.

In one embodiment represented in FIGS. 4 to 13, the channel (12) has a support wall having an element, called a moving baseplate (3), that is moveable relative to the fixation head (11). Said moveable baseplate (3) has a part (31) suitably in form of a spherical surface positioned in a complementary contact in a housing formed in the wall of the channel (12). By virtue of said spherical contact, the moving baseplate (3) has a certain freedom of rotation around the center of its complementary spherical part (31). Said moving baseplate has in particular a certain clearance (a3) in rotation around an axis (d3) that is substantially perpendicular to the longitudinal axis(d12) of the channel and to the direction of support of the clamping means. On its face, that is the support face (32), in contact with the bar, the moving baseplate has a shape complementary to the external surface of said bar, for example in the form of a cylindrical portion, that provides a good contact surface when clamped.

On its part (31) in the form of a spherical surface, the moving baseplate (3) can have one or a plurality of formal irregularities (310) that are adapted to cooperate with one or a plurality of formal irregularities of the housing of the fixation head(11) to form a stop limiting the clearance in rotation of the moving base plate. Said formal irregularities (310) can be, for example, a pin protuding from the moving baseplate and co-operating with a larger dimensioned cavity formed on the complementary contact surface. Said stop, for example, tends to prevent excessive turning of the moving baseplate and assures that it properly presents its support facing the bar. Thus, in the embodiment represented in FIGS. 4 to 7, the formal irregularity (310) is a pin disposed under the spherical part (31) of the moving baseplate (3), and in the embodiment represented in FIGS. 8 and 9, the formal irregularity (310) is a pin disposed on the rear of the moveable baseplate (3). Likewise, in the embodiment represented in FIGS. 12 and 13, the formal irregularity (310) is a pin, having an oblong cross-section, disposed on the front of the moving baseplate. The dimensions of the cavities adapted to cooperate with the formal irregularities (310) in the form of a pin exceed by at least about 20 to 30 mm the dimensions of said formal irregularities (310) at least along the axis of rotation (d3) of the moving baseplate (3) so as to enable there to be an angular clearance of the moving baseplate without permitting a complete rotation of same.

Figure 10:
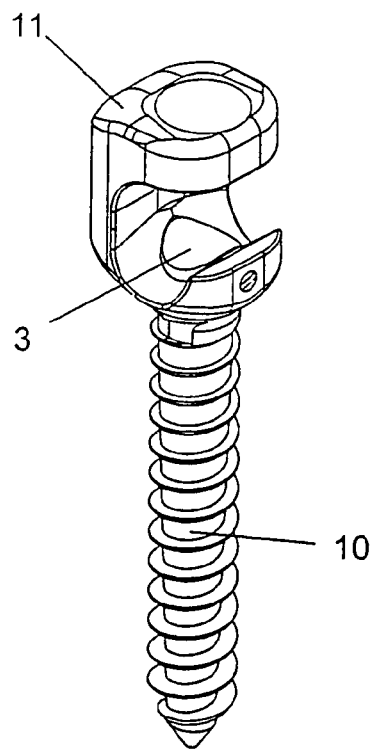
FIGS. 10 and 11 are, respectively, a perspective view and a sectional view of an implant with a fixed head according to a third embodiment of this invention.
Figure 11:
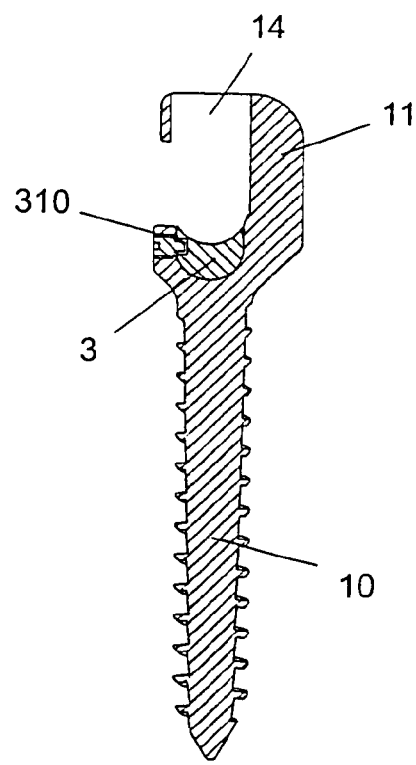
Figure 12:
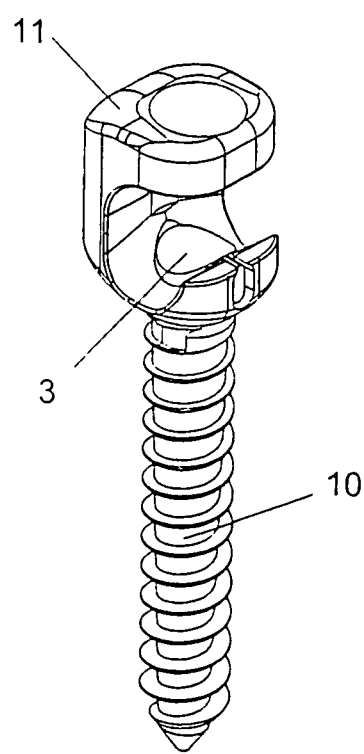
FIGS. 12 and 13 are, respectively, a perspective view and a sectional view of an implant with a fixed head according to a fourth embodiment of this invention.
Figure 13:
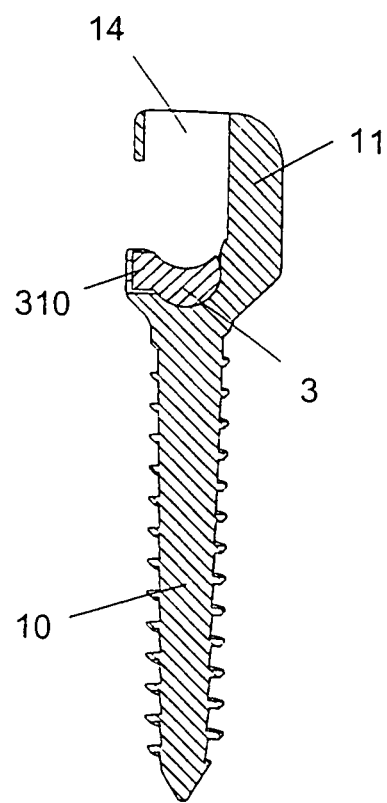

In the embodiment represented in FIGS. 10 and 11, the formal irregularities (310) are a cylindrical drilled hole disposed in the front of the moving baseplate (3) and adapted to cooperate with the cylindrical head of a pin held in a drilled hole disposed on the fixation head, the dimensions of the cylindrical drilled hole being greater than those of the head of the pin by at least about 20 to 30 mm, at least along the axis of rotation (d3) of the moving baseplate (3). In this fashion, the pin enables the moving baseplate (3) to turn around said axis (d3) while holding it in the complementary cavity housed in the wall of the channel (12).

With regard to the bar (2), the inside surface of the channel (12) is of sufficient dimensions to enable the bar to have a certain clearance (a2) in rotation around one or a plurality of axes not parallel to the longitudinal axis of the bar or, in particular, perpendicular to this longitudinal axis.

At its end on the bar side, the clamping screw (41) constitutes a moving element, called the support head (42), articulated by a ball and socket connection. The screwing of the clamping screw (41) provokes the pressing of said support head (42) on the flat of the bar (2) through one moving clamping face (420) of the moveable clamping system. Said ball and socket connection allows a certain clearance of the support head (42) relative to the clamping screw (41) in rotation around the center of said ball and socket connection.

By a rotation around at least one axis parallel to the axis of rotation (d3) of the moving baseplate (3), the moving support face (420) can thus be permanently adjusted to the position of the bar and the moving baseplate.

Said ball and socket connection also enables the support face to remain in contact with the bar without sliding over it, which avoids deterioration of the surfaces in contact, assures the blockage, and reduces the risk of residual stresses.

Thus, it can be understood, that the bar can be inserted and blocked in different angular positions inside the channel (12), while providing a flat contact surface both with the clamping means and with the wall of the channel by means of the moving baseplate (3). Said polyaxial angular clearance thus allows inserting the bar more easily and obtaining a clamping of the bar in its most natural position relative to the implants, which reduces or eliminates the stresses that could remain in the device after clamping. Furthermore, the clamping forces concur directly with blocking without necessarily countering the rigidity of the bar. The reliability of the blocking is thus improved.

Figure 1:
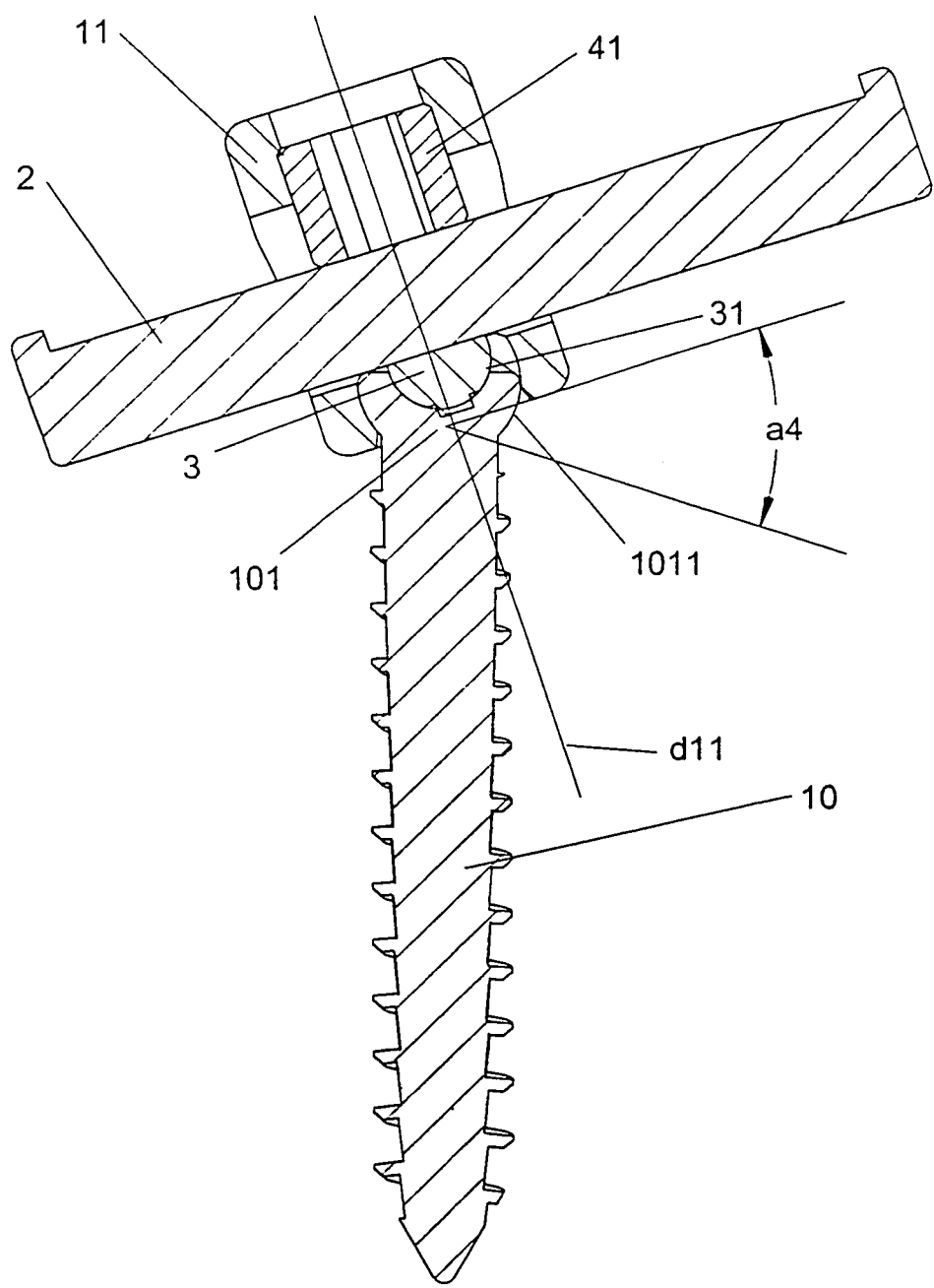
FIG. 1 is a sectional view of an implant according to this invention.
Figure 2:
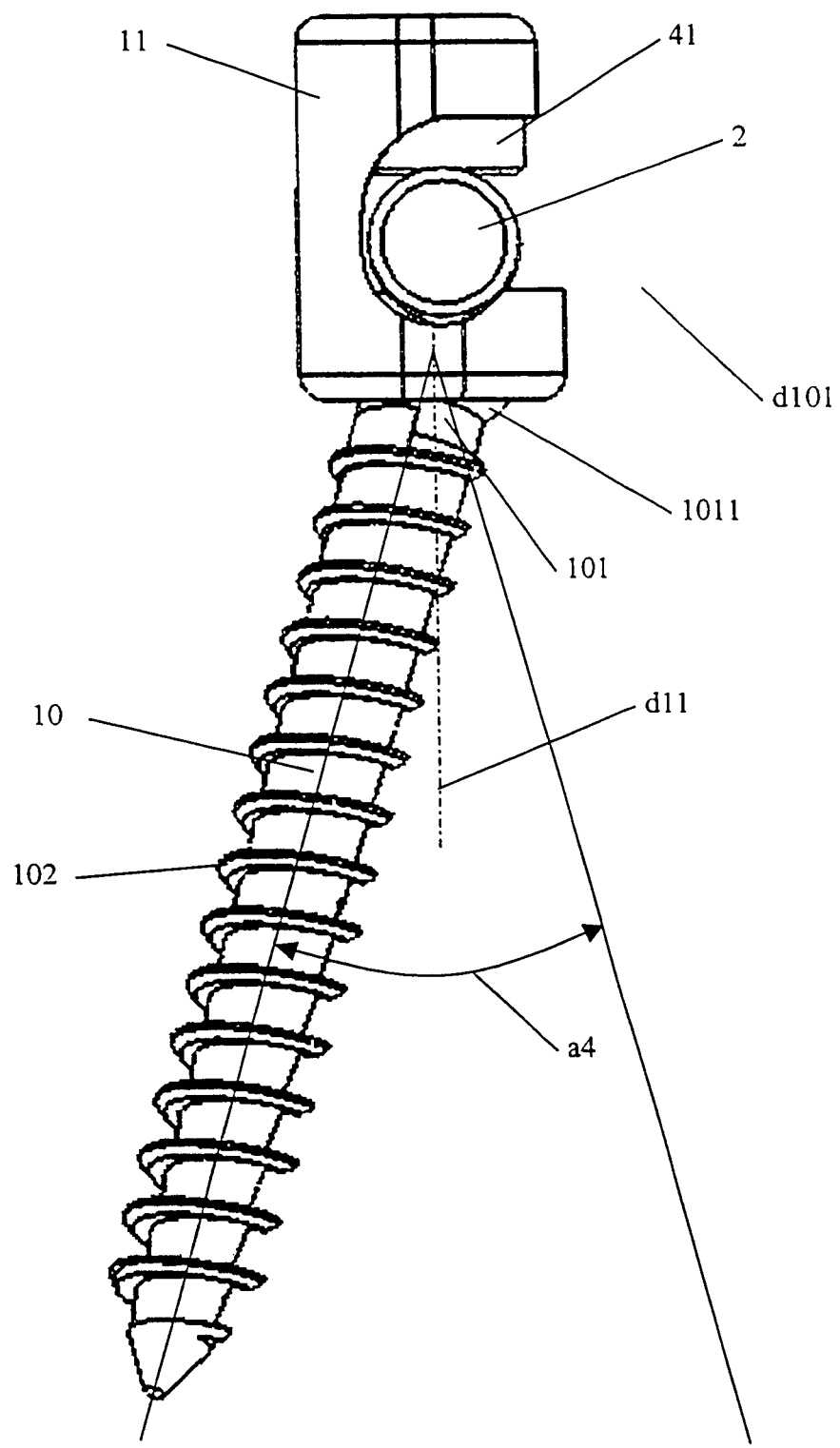
FIG. 2 is a side elevation of an implant according to this invention.
Figure 3:
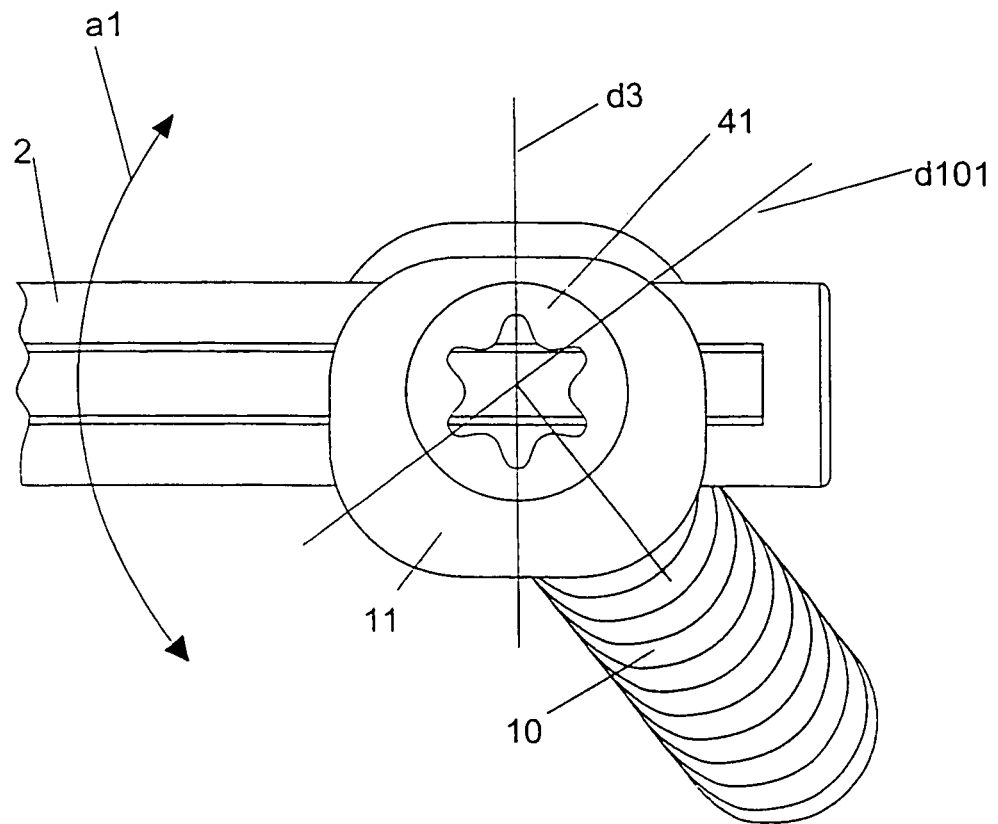
FIG. 3 is a top perspective view of an implant according to this invention.
Figure 4:
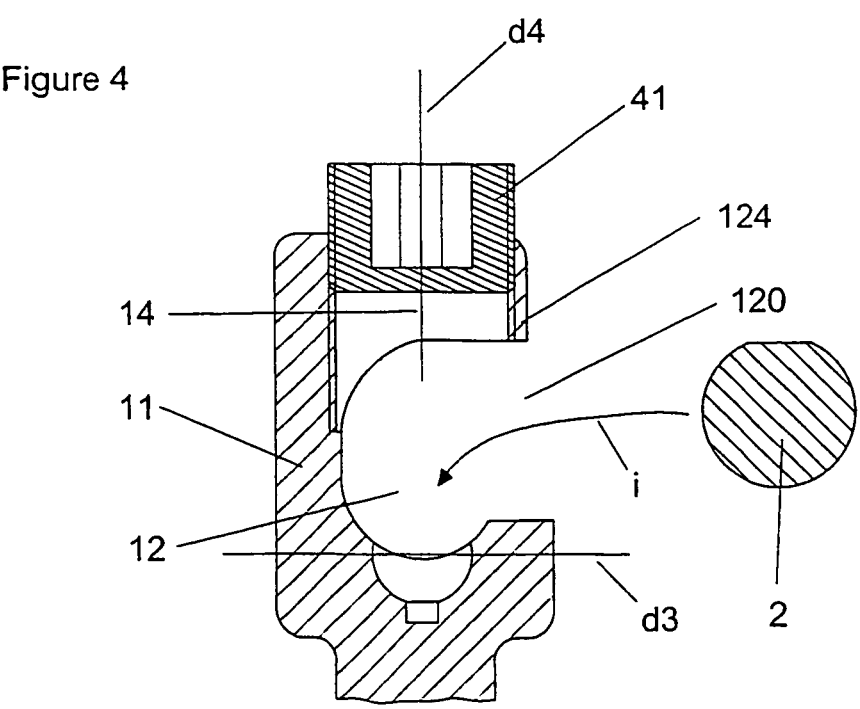
FIG. 4 is a sectioned partial side view of an implant with a fixed head during introduction of the bar, shown in section transverse to the bar.
Figure 5:
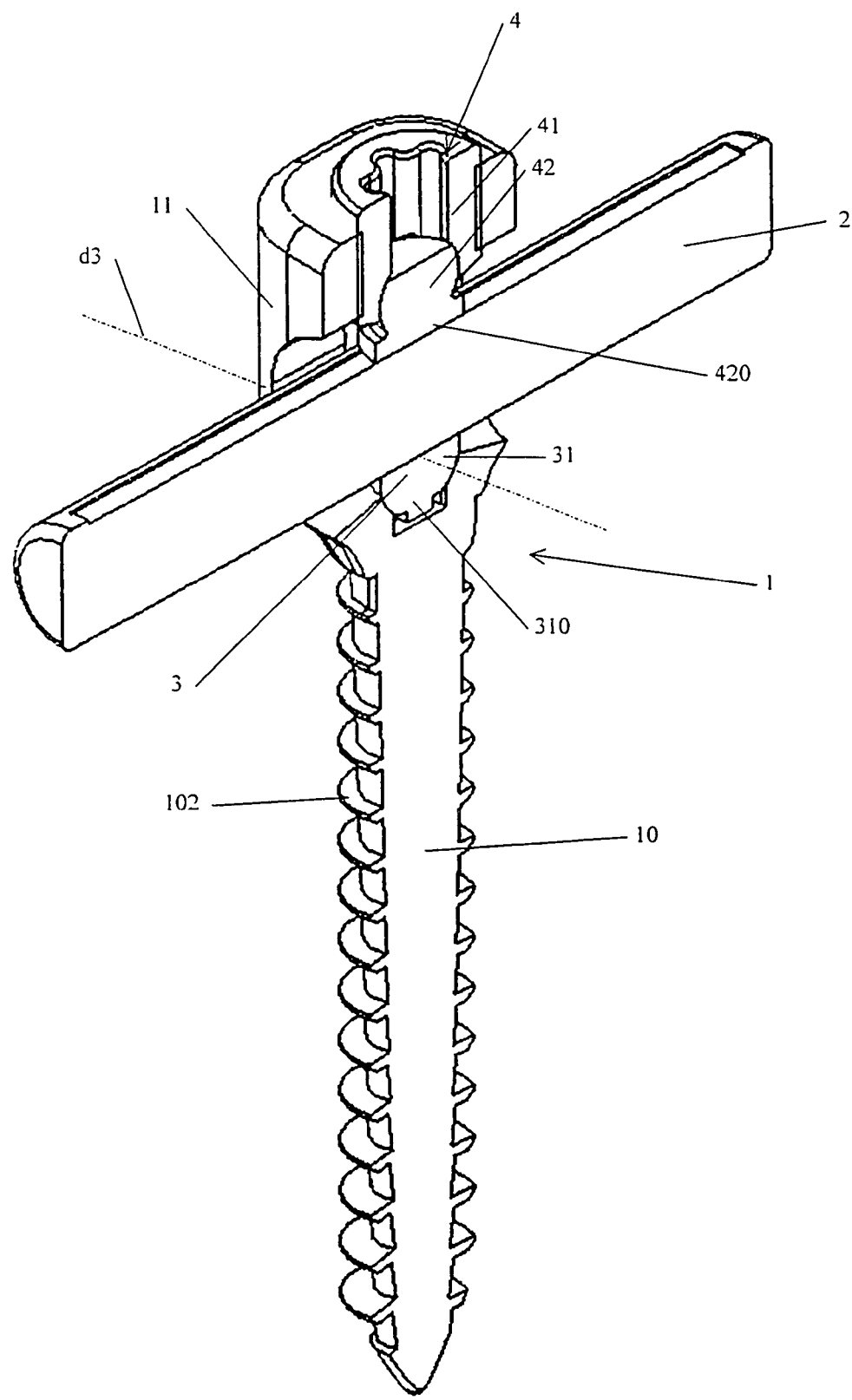
FIGS. 5 and 6 are perspective views of an implant with a fixed head, a bar and an osseous anchorage through screw with portions cut away along the axis of the bar, and transverse to the bar, respectively.
Figure 6:
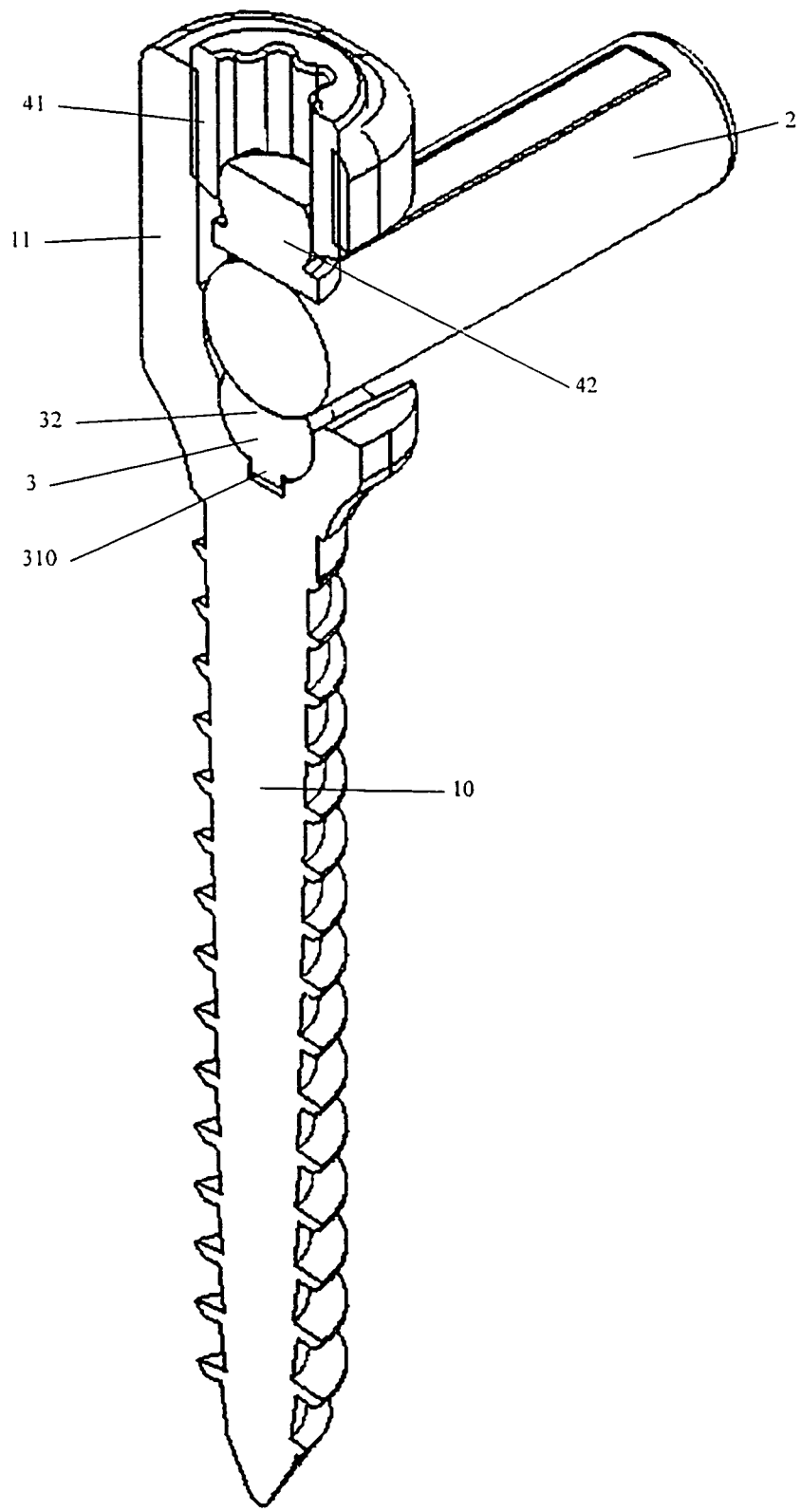

In an embodiment represented in FIGS. 1 to 3, the fixation head (11) is adapted to move relative to the osseous anchor (10) according to an articulation. This enables freedom in rotation around at least two axes not coincident with the longitudinal axis of the bar.

This articulation is realized by a complementary spherical contact disposed between the fixation head (11) and the end of the osseous anchor (10) remote from the osseous element, said end being designated as the rotation head (101). The rotation head comprises a part (1011) in form of a hemispherical portion widening in the direction of the fixation head (11); that is, by moving away from the osseous element. Said hemispherical portion (1011) is retained on the inside of the fixation head (11) by a complementary contact surface in a housing formed in said fixation head and narrowing itself towards the osseous anchor. Said housing communicates with the channel (12) where it is open in its part situated opposite to the clamp. The spherical nature of these contact surfaces thus enable a rotation of the fixation head and the osseous anchor relative to each other, about the center of said surface (1011) that has a hemispherical form.

Said rotations enable, in particular, unlimited clearance (a1) of the fixation head relative to the osseous anchor, in rotation around an axis(d11), called the axis of rotation of the head, that is not parallel, indeed not even perpendicular to the longitudinal axis of the bar or of the channel and passing through the center of the hemisphere (1011) of the rotation head (101).

These rotations also enable a certain clearance (a4) of the fixation head relative to the osseous anchor, in rotation around an axis that is substantially perpendicular to the axis(d11) of rotation of the head and passing through the center of the hemisphere (1011) of the rotation head (101).

In this embodiment, a mobile base (3) similar to that hereinbefore described is borne by the rotation head (101) in a housing formed on the face opposite to the bar.

At the time of attaching the clamp, the clamping screw (41) co-operates by its threading with the drilling (14) of the fixation head (11) to the hold the bar (2). The bar presses against the moving baseplate (3). The moving baseplate (3) leans on the rotation head (101), which is retained by the housing of the fixation head (11). Clamping of these surfaces among themselves produces an interlocking of the set of these parts relative to each other.

It is well understood that in this manner an implant is provided, whose fixation head, prior to affixing of the clamp, is moveable relative to the osseous anchoring part, while being fixed to the bar after assembly. The fixation head (11) can thus be tilted within a pre-determined clearance relative to the exterior surface of the osseous element and can pivot freely around an axis extending from said osseous surface.

Once the implant is anchored in the osseous element, it is thus still possible to adjust the position of the fixation head in order to enable the bar to keep or to resume its shape, which reduces the risks of residual stresses and permits easy introduction of the bar into diverse positions of this bar and implants. Once the bar is introduced and the whole device assembled, it is thus possible to fix said positions by virtue of the clamp. As clamping can be achieved in the most natural position of the pin, the clamping forces are concentrated such that they achieve fixation reliability. In particular, these clamping forces do not risk, or the risk thereof is minimal, introducing residual stresses or movements relative to the position selected by the surgeon.

In one embodiment of this invention, the clamping means (4) need not comprise a support head (42) on the ball and socket connection, in particular if the tilting of the fixation head (11) is sufficiently close to that of the bar (2) to assure a planar contact between the clamping screw (41) and the flat of the bar.

In the embodiments represented in the figures, the fixation head (11) of the implant (1) has a square external section that enables easy implantation of the implant (1) into a vertebra using a suitable tool. In other respects, the head passing above the channel (12), makes it easy to subsequently reposition the implant (1) in the vertebra after the bar (2) has been introduced into the channel (12).

It should be clear to the specialist in the art that the present invention enables embodiments in many specific forms without moving it away from the field of application of the invention as claimed. Consequently, the present embodiments must be considered illustrative, but can be modified in the field defined by import of the attached claims and the invention should not be limited to the details provided above.

The invention claimed is:

1. An osseous anchorage implant adapted to receive and clamp a bar having a longitudinal axis, the implant comprising:
    an osseous anchor; and
    a fixation head, the fixation head comprising
        a channel comprising
            a longitudinal axis,
            openings at each end of the longitudinal axis of the channel, and
            an inside surface configured for a rotational clearance of the bar about at least two axes of the channel not parallel to the longitudinal axis of the channel and not parallel to the longitudinal axis of the bar, including a support wall adapted to support the bar in any orientation within the rotational clearance of the bar independently of the orientation of the osseous anchor,
        a clamp mount,
        a clamp having a support head adapted to hold the bar against the support wall, and
        a lateral opening along the longitudinal axis of the channel, the lateral opening flanking the clamp mount and adapted for lateral insertion of the bar at a point along the longitudinal axis of the bar.

2. An implant according to claim 1 in which the inside surface of the channel is configured for a rotational clearance of the bar about plural axes of the channel not parallel to the longitudinal axis of the channel.

3. An implant according to claim 1 in which the support wall comprises a moveable baseplate.

4. An implant according to claim 3 in which the baseplate comprises a support face adapted for complementary contact with a surface of the bar.

5. An implant according to claim 4 in which the baseplate further comprises a portion shaped substantially as a portion of a sphere, which spherically shaped portion is disposed in a substantially complementary housing in the fixation head.

6. An implant according to claim 3 in which the baseplate has an axis of rotation not parallel to the longitudinal axis of the channel.

7. An implant according to claim 6 in which the clamp has a longitudinal axis, and the axis of rotation of the baseplate also is not parallel to the longitudinal axis of the clamp.

8. An implant according to claim 7 in which the support head articulates at an end of the clamp about an axis substantially parallel to the axis of rotation of the baseplate.

9. An implant according to claim 8 in which the support head articulates at a ball and socket joint.

10. An implant according to claim 6 in which the baseplate further comprises a stop limiting rotation about the axis of rotation.

11. An implant according to claim 10 in which the stop comprises a pin protruding from the baseplate into a cavity formed in the fixation head.

12. An implant according to claim 10 in which the stop comprises a pin protruding from the fixation head into a cavity formed in the baseplate.

13. An implant according to claim 1 in which the support head articulates at an end of the clamp.

14. An implant according to claim 1 in which the clamp comprises a threaded body and the clamp mount comprises a tapped hole.

15. An implant according to claim 1 in which the osseous anchor comprises a hook.

16. An implant according to claim 1 in which the osseous anchor comprises a screw.

17. An implant according to claim 16 in which the fixation head is fixed to the anchor with the longitudinal axis of the channel substantially perpendicular to a longitudinal axis of the screw.

18. An implant according to claim 1 in which the inside of surface of the channel has a shape comprising two head to tail truncated cones with minor baseplates facing each other and joined to each other.

19. An implant according to claim 18 in which the head to tail truncated cones are joined to each other by a cylindrical part.

20. An implant according to claim 1 further adapted to receive and clamp a bar having a clamping surface along at least a portion of the longitudinal axis of the bar, in which the support head comprises a contact surface complementary to the clamping surface of the bar.

21. An implant according to claim 20 in which the contact surface of the support head is flat.

22. An implant according to claim 1 in which the fixation head is movable relative to the anchor.

23. An implant according to claim 22 in which the fixation head is movable relative to the anchor about two axes not coincident with the longitudinal axis of the bar.

24. An osseous anchorage implant adapted to receive and clamp a bar having a longitudinal axis, the implant comprising:
   an osseous anchor comprising a rotation head having a first housing; and
   a fixation head, the fixation head comprising
      a second housing adapted to receive the rotation head;
      a channel comprising
         a longitudinal axis,
         openings at each end of the longitudinal axis of the channel, and
         an inside surface configured for a rotational clearance of the bar about at least two axes of the channel not parallel to the longitudinal axis of the channel and not parallel to the longitudinal axis of the bar, including a baseplate having a support wall adapted to support the bar in any orientation within the rotational clearance of the bar independently of the orientation of the osseous anchor, the baseplate adapted to be disposed in the first housing,
      a clamp mount,
      a clamp having a support head adapted to hold the bar against the support wall, and
      a lateral opening along the longitudinal axis of the channel, the lateral opening flanking the clamp mount and adapted for lateral insertion of the bar at a point along the longitudinal axis of the bar.

25. An osseous anchorage implant adapted to receive and clamp a bar having a longitudinal axis, the implant comprising:
   an osseous anchor; and
   a fixation head, the fixation head comprising
      a channel comprising
         a longitudinal axis,
         openings at each end of the longitudinal axis of the channel, and
         an inside surface configured for a rotational clearance of the bar about at least two axes of the channel not parallel to the longitudinal axis of the channel and not parallel to the longitudinal axis of the bar, including an articulating support wall adapted to support the bar in any orientation within the rotational clearance of the bar independently of the orientation of the osseous anchor,
      a clamp mount,
      a clamp having an articulating support head adapted to hold the bar against the support wall, and
      a lateral opening along the longitudinal axis of the channel, the lateral opening flanking the clamp mount and adapted for lateral insertion of the bar at a point along the longitudinal axis of the bar.

* * * * *